United States Patent [19]

Spatola et al.

[11] Patent Number: 5,244,884
[45] Date of Patent: Sep. 14, 1993

[54] THIONATED ANALOGUES OF THYROTROPIN RELEASING HORMONE

[75] Inventors: Arno F. Spatola, Louisville, Ky.; Leszek Lankiewicz, Gdansk, Poland; Virender M. Labroo, Rockville; Stefan Vonhof, Bethesda, both of Md.

[73] Assignee: The Government of the U.S. of America as represented by the Sec. of the Dept. of Health & Human Services, Washington, D.C.

[21] Appl. No.: 963,026

[22] Filed: Oct. 19, 1992

Related U.S. Application Data

[63] Continuation of Ser. No. 549,172, Jul. 6, 1990, abandoned.

[51] Int. Cl.$^5$ .................. A61K 37/24; A61K 37/43
[52] U.S. Cl. ................................ 514/18; 530/331
[58] Field of Search ........................ 530/331; 514/18

[56] References Cited

U.S. PATENT DOCUMENTS

| 4,215,110 | 7/1980 | Lotti et al. |
| 4,426,378 | 1/1984 | Holaday |
| 4,608,365 | 8/1986 | Engel |

OTHER PUBLICATIONS

L. Lankiewicz, Abstract Form, 11th Am. Peptide Symposium, Jul. 1989 The Salk Institute, Univ. of Calif., San Diego.
Jean E. Rivier and Garland R. Marshall "Peptides", Chemistry, Structure and Biology, Proceedings of the 11th American Peptide Symposium, Jul. 1989, Calif.
Marian Kruscynski, Polish Journal of Chemistry "Synthesis of a TRH Analog with a C-Terminal Thioamide Group", 60, 95 (1986).
Experientia 41, (1985), M. Kruszynski et al.; "TRH analogue with C-terminal thioamide group."
The New England Journal of Medicine, Jul. 24, 1980, pp. 224-225.
Neurology 36, Sep. 1986, pp. 1218-1221.
Acta Physiol Scand, 1979, 106:83-86, F. Koivusalo et al., "The Effect of Centrally Administered TRH on Blood Pressure, Heart Rate and Ventilation in Rat".
Neuroendocrinology 35:173-177 (1982); Bao L. Tsay et al.; "Effects of Intracerebroventricular Administration of Thyrotrophic-Releasing Hormone on Cardiovascular Function in the Rat".
Brain Research Bulletin, vol. 6, pp. 13-17, J. P. Farber et al.; "Effects on Breathing of Putative Neurotransmitters in the Rostral Hypothalamus of the Rat".
Progress in Neurobiology, vol. 12, pp. 291-312 (1979), G. Yarbrough.
Neuropeptides, vol. 8, pp. 63-70; (1986); A. L. Siren et al.

(List continued on next page.)

*Primary Examiner*—Howard E. Schain
*Attorney, Agent, or Firm*—Birch, Stewart, Kolasch & Birch

[57] ABSTRACT

There are disclosed thionated analogues of thyrotropin releasing hormone, having the formula:

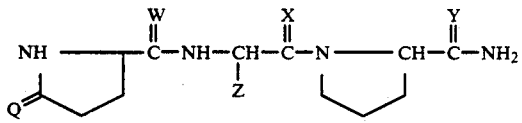

wherein,
Q, W, X and Y, same or different, are oxygen or sulfur, with the proviso that at least one of Q, W, X and Y is always sulfur;
Z is lower alkyl or (4-imidazolyl)methyl; and the pharmaceutically acceptable salts thereof. The disclosed compounds highly and selectively bind to TRH binding sites in animal tissues, and their utility in treating a variety of diverse physical conditions is disclosed. Pharmaceutical compositions containing the compounds are also disclosed.

10 Claims, No Drawings

OTHER PUBLICATIONS

Stefan Vonhof et al., European Journal of Pharmacology, vol. 164, pp. 77-83, (1989).
Geoffrey Metcalf et al., Elsevier Biomedical Press, 3, pp. 193-206, (1982).
Ruth F. Nutt et al., J. Med. Chem., vol. 24, pp. 692-698, (1981).
D. Brewster et al., Neuropeptides, vol. 1, pp. 153-165, (1981).
K. Funatsu et al., Peptides, vol. 6, pp. 563-566 (1985).
E. F. Hawkins et al.; Life Sciences, vol. 36, pp. 601-611 (Pergamon Press).
N. Ogawa et al., Peptides, vol. 3, pp. 669-677 (1982).
Geoffrey Metcalf et al., Regulatory Peptides, vol. 2, pp. 277-284 (1981).
N. A. Sharif, TIPS-Mar. 1985, pp. 119-122.
T. McIntosh, et al., Am. J. Physiol., vol. 254, pp. R785-R792.
F. Brambilla et al., Neuropsychobiology, vol. 15, pp. 114-121 (1986).
John N. Whitaker et al., Annals of Nuerology, vol. 22, No. 4 (1987).
H. N. Bhargava, Psychopharmacology, vol. 68, pp. 185-189 (1980).
The Lancet, Jan. 27, 1979, pp. 210-211.
The Lancet, Feb. 23, 1980 pp. 424-425.
L. Koskinen, Annals N.Y. Academy of Sciences, 1989, Section VIII, pp. 353-387.
T. Munsat et al.; Annals of N.Y. Acad. of Sciences, pp. 388-475.

THIONATED ANALOGUES OF THYROTROPIN RELEASING HORMONE

This application is a continuation of application Ser. No. 07/549,172 filed on Jul. 6, 1990, now abandoned.

FIELD OF THE INVENTION

The present invention relates to thionated analogues of thyrotropin releasing hormone (TRH) type compounds, which highly, selectively and differentially bind to TRH receptor binding sites in animal tissues. The invention is further concerned with providing treatment methods for a variety of adverse physical conditions with the disclosed compounds, as well as providing pharmaceutical compositions containing the same compounds. The invention is also concerned with providing a method of detecting TRH receptor sites present in animal tissues.

BACKGROUND OF THE INVENTION

Thyrotropin releasing hormone is a tripeptide hormone (L-pyroglutamyl-L-histidyl-L-proline-amide) found in the hypothalamus as well as in other parts of the brain. TRH has multiple biological effects that are mediated through its interactions with various receptors to the peptide. Some, but not all of these actions involve its ability to cause the release of thyrotropin stimulating hormone (TSH), especially from the anterior pituitary tissue of higher mammals. Other properties that TRH has been disclosed to possess include thyroid stimulating, antidepressant and lactation promoting activities [U.S. Pat. No. 3,931,139; Science, 178, 417–418 (1972). Furthermore, its use in the treatment of circulatory shock and/or central nervous system (CNS) ischemic damage [U.S. Pat. No. 4,426,378], as well as in the amelioration of symptoms associated with amyotrophic lateral sclerosis (ALS) [U.S. Pat. No. 4,608,365] and hypertension [U.S. Pat. No. 4,215,110] has been disclosed.

A method of synthesis for one of the thionated TRH analogues encompassed hereby (L-pyroglutamyl-L-histidyl-L-prolinethioamide) was reported by M. Kruszynski in the "Polish Journal of Chemistry", Vol. 60, p. 95 (1986). It was also reported by Kruszynski that the compound exhibited TRH receptor binding affinity as well as a TSH releasing activity matching that of natural TRH. However, there was no disclosure of the compounds ability to highly and selectively bind to TRH receptor sites in the cortex, as compared with its binding to TRH receptor sites in the pituitary. The compound is encompassed by Formula I herein, but not by Formula II.

Several of the thionated TRH analogues encompassed hereby are disclosed by Lankiewicz et al in "Peptides Chemistry, Structure and Biology", Proceedings of the Eleventh American Peptide Symposium, Jul. 9–14, 1989, La Jolla, Calif., USA, p. 976–977 (1990). The compounds are disclosed to possess TSH-releasing activity in vitro. The Lankiewicz et al reference is expressly incorporated by reference.

SUMMARY OF THE INVENTION

One object of the present invention is to provide compounds which are useful in treating a variety of diverse physical conditions such as depression, circulatory shock, ALS, spinal cord injury and hypertension among others. A second object of the present invention is to provide medical practitioners with compounds which can be used as diagnostic agents in the evaluation of hyperthyroid and hypothyroid states. A third object of the present invention is to provide compounds useful in a method for determining the presence of TRH receptor sites in animal tissues.

It is also an object of the present invention to provide pharmaceutical compositions containing the active compounds of the present invention.

Achievement of the above objects is made possible herein by utilizing the Formula I and Formula II thionated analogues of TRH disclosed herein.

Compounds encompassed hereby which are useful in the various methods and compositions disclosed herein include the following:

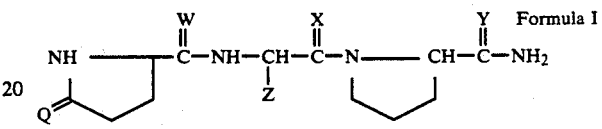

wherein,

Q, W, X and Y, same or different, are oxygen or sulfur, with the proviso that at least one of Q, W, X or Y is always sulfur; Z is lower alkyl or (4-imidazolyl)methyl; and the pharmaceutically acceptable salt thereof.

Of the compounds encompassed by the above Formula I, the following compounds are both novel and preferred in the present invention:

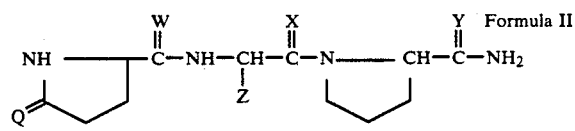

wherein,

Q, W, X and Y, same or different are oxygen or sulfur, with the proviso that at least one of Q, W or X is always sulfur; Z is lower alkyl or (4-imidazolyl)-methyl; and the pharmaceutically acceptable salts thereof.

The following glossary of terms is provided to remove any ambiguity which may exist as to their meanings.

The term "lower alkyl" as used herein means a straight or branched alkylic radical containing 1–8 carbon atoms. Exemplary of such alkylic radicals are methyl, ethyl, propyl, 2-propyl, butyl, isobutyl, pentyl, isopentyl, hexyl, heptyl, octyl or the like.

The term "(4-imidazolyl)methyl" as used herein refers to an organic radical having the following structure.

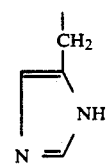

The term "pharmaceutically acceptable salt" as used herein includes non-toxic pharmaceutically acceptable salts of the compounds of Formulae I or II disclosed herein with organic moieties such as acetate, trifluoroacetate, oxalate, valerate, oleate, laurate, benzoate, lactate, tosylate, citrate, maleate, fumarate, succinate, tartrate naphthalate, and the like; and such inorganic moieties as Group I (i.e., alkali metal salts), Group II (alkaline Earth metal salts), ammonium and protamine, zinc, iron and the like with counter ions such as chloride, bromide, sulfate, phosphate and the like, as well as the organic moieties referred to above.

The term "pharmaceutically acceptable carrier" as used herein, includes, for example, pharmaceutically acceptable carriers such as the following: solid carriers such as lactose, magnesium stearate, terra alba, sucrose, talc, stearic acid, gelatin, agar, pectin, acacia or the like; and liquids such as vegetable oils, arachis oil and sterile water, or the like. However, this listing of pharmaceutically acceptable carriers is not to be construed as limiting to the present invention.

DETAILED DESCRIPTION OF THE INVENTION

The following detailed description is provided to further aid those desiring to practice the present invention. Included in the following description are discussions relating to different aspects of the present invention as well as specific examples related to the synthesis of certain compounds herein encompassed. The following discussions and examples should not, however, be deemed to unduly limit the present invention, since many aspects of the present invention discussed below may be slightly modified or changed by those of ordinary skill in the art without departing from the spirit or scope of the present invention. In this regard, it is further noted that the present invention is only to be limited by the scope of the claims appended hereto, and the equivalents thereof.

In order for any TRH analogue to prove clinically useful in the treatment of physical conditions, it is often thought necessary that some of the biological properties found in TRH must be eliminated from the analogue's therapeutic profile, while certain other TRH type properties should be enhanced. Realizing this factor, we, the present inventors (by changing the structure of the side chain and/or backbone of TRH) have significantly altered the selectivity of certain TRH analogues to a variety of TRH receptors in animal tissues. More specifically, we have found that by replacing one or more oxygens in the backbone amides of TRH with sulfur, there are produced selective analogues of TRH, which highly and selectively bind to different TRH receptors in animal tissues. Furthermore, we provide evidence herein for the first time, that the thionated analogues of TRH encompassed hereby, due to their preferential binding, constitute a class of therapeutically important compounds having utilities making them valuable candidates for clinical development.

The preferential binding of Formulae I and II compounds disclosed herein to different TRH receptors, we believe is essential to the present invention. This is due to the fact that the multiple actions of TRH have often made its use in therapeutic applications inappropriate, since heretofore there was no practical method to dissociate between the desired as opposed to the often undesired biological actions of the potent and ubiquitous endogenous hormone.

We also note that we have fortuitously discovered that applications of the thionation procedure disclosed herein to analogues of TRH that already possess some selectivity for TRH receptors (e.g., compounds such as pGlu-Nva-Pro-NH$_2$) leads to still further dissociations of biological responsiveness and thereby provides a further demonstration of the importance of the thionated analogues disclosed herein. Such a discovery is, of course, of value to all who are skilled in the art.

Equally important to the present invention is our finding that cortex and pituitary TRH receptors are likely to be distinct and structurally diverse biological molecules (since the compounds of Formulae I and II differentially bind thereto), because the multiple modes of TRH action can now be effectively separated and exploited, even at the level of regional differences in brain action.

The following discussions are divided into three separate sections, entitled as follows: COMPOUND SYNTHESIS; PHARMACOLOGY; and PHARMACEUTICAL COMPOSITIONS.

COMPOUND SYNTHESIS

The compounds of Formulae I and II encompassed hereby may be prepared from commercially available compounds utilizing techniques which are readily understood by those of ordinary skill in the art. Exemplary of such techniques are solution-phase methodologies such as described by Bodanszky, Klausner, Ondetti (1976). As such, the following Experimental Procedures utilized by the present inventors to provide compounds of Formulae I and II herein, is only exemplary of suitable methods and thus should not be considered to limit the present invention.

Experimental Procedures

Melting points were determined on a Thomas-Hoover apparatus and are uncorrected. Optical rotations were determined on a Perkin-Elmer 241 MC polarimeter. NMR spectra were recorded on a Varian XL-300 spectrometer and chemical shifts are reported in ppm ($\delta$ units). A Dionex D-300 amino acid analyzer equipped with a Dionex CP-3 program was employed for amino acid analysis (AAA) of peptides.

Thin layer chromatographic (TLC) analysis was performed on Merck Kieselgel 60-F$_{254}$ plates and R$_f$ values are given for the solvent systems indicated. Reaction products were visualized by one or more of the following procedures: (1) exposure to iodine vapors, (2) UV-fluorescence, (3) 0.1% ninhydrin in ethanol or (4) 20% (NH$_4$)$_2$SO$_4$ in H$_2$O/4% H$_2$SO$_4$.

Analytical RP-HPLC was performed on Vydac 4.6×250 mm ODS column on a Hitachi 655A system equipped with L-5000 controller, D-2000 integrator, and a variable wavelength UV detector. The solvent system was composed of H$_2$O/0.05% TFA (A) and CH$_3$CN/0.05% TFA (B).

Column chromatography was carried out under low pressure (according to Still et al (1978), using Merck grade 60 silica 230–400 mesh. Gel permeation chromatography on a Sephadex G-10 column (2.8×62 cm) and/or preparative reversed phase chromatography on a Vydac ODS column (2.5×25 cm) yielded the final products.

Triethylamine, 1-hydroxybenzotriazole (HOBt), and Lawesson's reagent were products of Aldrich Chemical Co. 1-Ethyl-3-(3-dimethylaminopropyl)-carbodiimide (EDC) were obtained from Sigma Chemical Co. HPLC grade solvents were purchased from either Baxter or CMS. Deuterated solvents were obtained from MSD Isotopes.

Amino acid derivatives were purchased from Bachem (Torrance) or Bachem Bioscience (Philadelphia). N-tert-butyloxycarbonyl-L-proline amide was prepared from proline amide and di-tert-butyl dicarbonate according to Moroder et al (1976). The 2,4,5-trichlorophenyl ester of L-pyroglutamic acid was synthesized according to Anderson et al (1967). Tert-butyl ester of L-pyroglutamic acid was obtained from L-pyroglutamic acid and isobutylene according to Hollosi et al (1972). L-proline thioamide from N-tert-butyloxycarbonyl-L-proline thioamide (N$^{im}$-dinitrophenyl)-L-histidyl-L-proline amide trifluoroacetate, and (N$^{im}$-dinitrophenyl)-L-histidyl-L-proline-2-thioamide tri-fluoroacetate were prepared by following the procedures of Kruszynski (1986).

Preparation 1

Tert-butyl ester of L-thiopyroglutamic acid (Top-OtBu)

The tert-butyl ester of L-pyroglutamic acid (1.85 g, 10 mmol) was dissolved in freshly distilled THF (50 ml). To the stirring solution was added Lawesson's Reagent (2.32 g, 5 mmol), and the mixture was stirred at room temperature until the starting materials were fully consumed (1 h, TLC control). Evaporation of solvent in vacuo followed by purification by flash chromatography using 10% ethyl ether in methylene chloride gave the title compound (1.98 g, 94%); $R_f$ 0.77 (methylene chloride/ethyl ether, 4:1), $R_f$ 0.62 (ethyl acetate/pyridine/acetic acid water, 54:10:3:5); m.p. 93°–96° C. (Andersen et al, 1986, m.p. 94°–96° C.), $[\alpha]^{25}D+9.7°$ (c 1.0, methanol) (Anderson et al, 1986, $[\alpha]D+10.3°$ (c 3.0, methanol)); $^{13}$C-NMR (CDCl$_3$, 17° C.) 168.6 (—COO—), 204.9 (—CSNH—).

Preparation 2

L-thiopyroglutamic acid (Top)

The tert-butyl ester of thiopyroglutamic acid (1.05 g, 5.4 mmol) was placed in a round-bottom flask, to which freshly prepared 4N HCl/dioxane (20 ml) was added. The solution was stirred for 1 h. Evaporation of solvent in vacuo and then crystallization of an oily residue from methanol/benzene/methylene chloride gave the title compound as a crystalline product (0.69 g, 89.0%): $R_f$ 0.15 (chloroform/methanol/acetic acid, 85:10:5), $R_f$ 0.65 (1- butanol/acetic acid/water, 4:1:1); m.p. 117°–118° C. (Andersen et al, 1986, m.p. 119°–120° C.; $[\alpha]^{25}D-15.8$ (c 2.0, acetone) (Andersen et al, 1986, $[\alpha]D-16.4$ (c 2.0, acetone)); MS (FAB) 146 (M+ +H); $^{13}$C-NMR (DMSO-d$_6$, 30° C.) 172.6 (—COOH), 204.8 (—CSNH—).

Preparation 3

2,4,5-Trichlorophenyl ester of L-thiopyroglutamic acid (Top-OTcp)

The title compound was synthesized from 2,4,5-trichlorophenyl ester of L-pyroglutamic acid (0.31, 1 mmol) and Lawesson's Reagent (0.23 g, 0.5 mmol) according to the procedure given for Preparation 1. Flash chromatography using 5% ethyl ether in methylene chloride followed by recrystallization from ethyl acetate/hexane gave 0.23 g (74.1%) of the title compound $R_f$ 0.71 (chloroform/methanol/acetic acid, 85:10:5), $R_f$ 0.76 (ethyl ether-methylene chloride, 1:6); m.p. 113°–116° C.; $[\alpha]^{25}D+5.3$ (c 2.0, DMF); MS (FAB) 324 (M+ +H); $^{13}$C NMR (DMSO-d$_6$, 30° C.) 165.8 (—COO—), 204.5 (—CSNH—).

Preparation 4

N-tert-butyloxycarbonvl-L-proline thioamide (Boc-Pro [CSNH]-H)

The title compound was prepared from N-tert-butyloxycarbonyl-L-proline amide (1.07 g, 5 mmol) and Lawesson's Reagent (1.16 g, 2.5 mmol) by following the procedure for Top-OtBu in Preparation 1. Flash chromatography using 20% ethyl ether in methylene chloride followed by recrystallization from acetone gave the title compound (0.95 g, 82.3%) as pure white crystals: m.p. 193°–195° C. (decomp.) (Kruszynski, 1986, m.p. 195°–197° C. (decomp.)); $[\alpha]^{25}D-70.1°$ (c 1.0, ethanol) (Kruszynski, 1986, $[\alpha]^{25}D-73.2°$, (c 1.0, ethanol)); $R_f$ 0.56 (chloroform/methanol/water, 100:50:4); $^{13}$C-NMR (DMSO-d$_6$, 30° C.), 152.8 (—COO—), 208.5 (—CSNH$_2$).

Preparation 5

L-Thiopyroglutamyl-(N$^{im}$-dinitrophenyl)-L-histidyl-L-proline amide (Top-His(DNP)-Pro-NH$_2$)

Method A (coupling with EDC)

To a flask containing the compound of Preparation 2 (0.145 g, 1 mmol) was added dimethylformamide (5 ml) and (N$^{im}$-dinitrophenyl)-L-histidyl-L-proline amide trifluoroacetate (0.53 g, 1 mmol), followed by HOBt (0.15 g, 1 mmol). The flask was then cooled to 0° C. After stirring 5 min, triethylamine (0.14 g, 1 mmol) and EDC (0.2 g, 1.05 mmol) were added. Stirring was continued at 0° C. for 3 h and proceeded for 16 h at room temperature.

The solvent was removed in vacuo and residue was partitioned in a separatory funnel between ethyl acetate (50 ml) and 5% NaHCO$_3$ (20 ml). The organic layer was washed with 5% NaHCO$_3$ (2×20 ml), H$_2$O (1×20 ml) and saturated NaCL (1×20 ml). The ethyl acetate fraction was then dried over Na$_2$SO$_4$, filtered and stripped to leave an orange foam. The crude protected tripeptide was purified by flash chromatography using gradient 5–10% methanol in methylene chloride. Fractions containing desired compounds were pooled and stripped to leave yellow powder (0.41 g, (76.3%); m.p. 164°–165° C.; $[\alpha]D+25.6°$ (C=0.43; DMF); MS (FAB) 545 (M+ +H); $R_f$ 0.52 (ethyl acetate/acetone/acetic acid/water, 5:3:1:1), $R_f$ 0.41 (1-butanol/acetic acid/water, 4:1:1).

Method B (coupling with active ester)

To a flask containing the compound of Preparation 3 (0.35 g, 1.1 mmol), dimethylformamide (5 ml), (N$^{im}$-dinitrophenyl)-L-histidyl-L-proline amide trifluoroacetate (0.53 g, 1 mmol) and HOBt (0.15 g, 1 mmol) were added. The flask was then cooled to 0° C. and pH was adjusted to 8.0–8.2 with triethylamine (0.16 ml, 1.1 mmol). Stirring was continued at 0° C. for 1 h and proceeded for 16 h at room temperature.

The reaction mixture was worked up according to the procedure given in method A. The product was yellow powder (0.47 g, 86.1%); m.p. 160°–162° C.; $[\alpha]D +8.5°$ (C=0.79; DMF); $R_f$ 0.52 (ethyl acetate/acetone/acetic acid/water, 5:3:1:1), $R_f$ 0.41 (1-butanol/acetic acid/water, 4:1:1).

Preparation 6

L-thiopyroglutamyl-($N^{im}$-dinitrophenyl)-L-histidyl-L-proline thioamide (Top-His(DNP)-Pro [CSNH]H)

Method A (coupling with EDC)

The title compound was prepared from L-thiopyroglutamic acid (0.145 g, 1 mmol) and ($N^{im}$-dinitrophenyl)-L-histidyl-L-proline thioamide trifluoroacetate (0.55 g, 1 mmol) by following the procedure given in method A of Preparation 5. The title compound was obtained as a yellow powder (0.39 g, 70.6%); m.p. 155°–157° C. (decomp.); $R_f$ 0.68 (ethyl acetate/acetone/acetic acid/water, 5:3:1:1), $R_f$ 0.47 (1-butanol/acetic acid/water 4:1:1).

Method B (coupling with active ester)

The title compound was obtained from 2,4,5-trichlorophenyl ester of L-thiopyroglutamic acid (0.35 g, 1.1 mmol) and ($N^{im}$-dinitrophenyl)-L-histidyl-L-proline thioamide trifluoroacetate (0.55 g, 1 mmol) according to the procedure given in method B of Preparation 5. Work up yielded the title compound as a yellow powder (0.48 g, 80%); $r_f$ 0.68 (ethyl acetate/acetone/acetic acid/water, 5:3:1:1), $R_f$ 0.47 (1-butanol/acetic acid/water, 4:1:1).

Preparation 7

L-pyroglutamyl-($N^{im}$-dinitrophenyl)-L-histidyl-L-proline thioamide (Glp-His(DNP)Pro [CSNH]H The title compound was prepared from 2,4,5-trichlorophenyl ester of L-pyroglutamic acid (0.33 g, 1.1 mmol) and ($N^{im}$-dinitrophenyl)-L-histidyl-L-proline thioamide trifluoroacetate (0.55 g, 1 mmol) according to the procedure with active ester (method B) given for the synthesis of Preparation 5. Purification by flash chromatography gave the protected title tripeptide (0.36 g, 65.5%) m.p. 165°–168° C. (decomp.); $R_f$ 0.54 (ethyl acetate/acetone/acetic acid/water, 5:3:1:1), $R_f$ 0.43 (1-butanol/acetic acid/water, 4:1:1).

Preparation 8

N-tert-butyloxycarbonyl-L-norleucyl-L-proline amide (Boc-Nle-Pro-NH$_2$)

To a flask containing L-proline amide (1.14 g, 10 mmol) was added dimethylformamide (5 ml), methylene chloride (5 ml), and N-tert-butyloxycarbonyl-L-norleucine (2.32 g, 10 mmol), followed by HOBt (1.53 g, 10 mmol). The flask was then cooled to 0° C. After stirring 5 minutes, EDC (1.92 g, 10 mmol) was added. Stirring was continued at 0° C. for 3 hours and the coupling reaction proceeded for 16 hours at room temperature.

The solvent was removed in vacuo and residue was partitioned in a separatory funnel between ethyl acetate (100 ml) and 5% NaHCO$_3$ (50 ml). The organic layer was washed with 5% NaHCO$_3$ (1×50 ml), H$_2$O (1×50 ml), 1N HCl (1×50 ml), 5% NaHCO$_3$ (1×50 ml). The ethyl acetate fraction was then dried over Na$_2$SO$_4$, filtered and stripped to leave white powder. Recrystallization from ethyl acetate/hexane gave the title compounds as white crystals (3.05 g, 93%): oil, [α]O −42.1° (C=0.96; DMF); $R_f$0.69 (chloroform/methanol/acetic acid, 85:10:5), $R_f$0.54 (chloroform/methanol, 9:1).

Preparation 9

L-norleucyl-L-proline amide hydrochloride (HCl·Nle-Pro-NH$_2$)

The N-tert-butyloxycarbonyl-L-norleucyl-proline amide (1 g, 3.05 mmol) was placed in a round bottom flask to which freshly prepared 4N HCl/dioxane (25 ml) was added. The solution was stirred for 1 hour. Evaporation of solvent in vacuo and then crystallization of an oily residue from methanol/ethyl ether gave the title compound as a crystal-line product (0.76 g, 95%); oil, [α]D −17.7° (C=1; DMF); $R_f$ 0.31 (1-butanol/acetic acid/water 4:1:1), $R_f$ 0.42 (1 butanol/acetic acid/water, 4:1:5, upper phase).

Preparation 10

L-pyroglutamyul-L-norleucyl-L-proline-amide (Glp-Nle-Pro-NH$_2$)

To a flask containing the product of Preparation 9 (0.53 g, 2 mmol), there was added dimethylformamide (5 ml) and the 2,4,5-trichlorophenyl ester of L-pyroglutamic acid (0.65 g, 2.2 mmol) followed by HOBt (0.31 g, 2 mmol). The flask was then cooled to 0° C. and the pH was adjusted to 8.0 to 8.2 with triethylamine (0.28 ml, 2.2 mmol). Stirring was continued at 0° C. for 1 hour and then for 16 hours at room temperature.

The solvent was removed in vacuo and the residue was partitioned in a separatory funnel with ethyl acetate (50 ml) and 5% NaCHO$_3$ (10 ml). The organic layer was washed with 5% NaHCO$_3$ (1×10 ml), H$_2$O (1×5 ml), 5% NaHCO$_3$ (1×10 ml), and saturated NaCl (1×10 ml). The ethyl acetate was then dried over Na$_2$SO$_4$, filtered and stripped to leave a white oil. Reversed phase chromatography (Vydac C$_{18}$, 7% CH$_3$CN in 0.05% TFA in H$_2$O, flow 3.5 ml/min) followed by lyophilization afforded the title compound as a white powder (0.39 g, 60.2%): m.p., oil, [α]D −16.0° (C=1.93; DMF); $R_f$0.45 (1-butanol/acetic acid/water, 41:1), $R_f$ 0.31 (chloroform/methanol/acetic acid, (85:10:5).

EXAMPLE 1

L-thiopyroglutamyl-L-histidyl-L-oroline amide ([Top$^1$]TRH)

To a stirring solution of the compound of Preparation 5 (0.11 g, 0.2 mmol) in DMF (5 ml) was added mercaptoethanol (1 ml). The solution was stirred for 1 h at room temperature. The solvent was removed in vacuo and the residue was placed on a column of silica gel and chromatographed using 30% methanol in methylene chloride Fractions containing the desired compound were pooled and stripped to leave a slightly yellow oil. This was purified by gel permeation chromatography (Sephadex G-10, 5% AcOH in H$_2$O, flow 10 ml/h) followed by reversed phase chromatography (Vydac C$_{18}$, 4% CH$_3$CN in 0.05% TFA in H$_2$O, flow 3.5 ml/min). Lyophilization yielded the title product, as a white, fluffy powder (31.2 mg, 41.3%). $R_f$0.45 (chloroform;methanol, 1:3), $R_f$ 0.38 (1-butanol/acetic acid/water/ethyl acetate, 1:1:1:1); [α]D 6.24° (C+1.73; DMF); MS (FAB) 379 (M++H); AAA: Glu (0.98), His (1.19), Pro (1.00); analytical RP-HPLC ($t_R$=9.62 min; a linear gradient of 5–35% B over 30 min at a flow rate of 1.0 ml/min); $^{13}$C-NMR (DMSO-d$_6$; 30° C.) 169.9 (—CO—His), 171.7 (—CO—Pro), 173.6 (—CONH$_2$), 204.9 (—CSNH—).

EXAMPLE 2

L-thiopyroglutamyl-L-histidyl-L-proline thioamide ([Top¹,Pro [CSNH]H³]TRH)

The title peptide was prepared from L-thiopyroglutamyl-(N$^{im}$-dinitrophenyl)-L-histidyl-L-proline thioamide (0.11 g, 0.2 mmol) and mercaptoethanol (1 ml) by following the procedure given for the synthesis of the compound of Example 1. Final purification by reversed phase chromatography (Vydac C$_{18}$, 9% CH$_3$CN in 0.05% TFA in H$_2$O, flow 3.5 ml/min) followed by lyophilization afforded the title product as a white powder (30.7 mg, 39.0%); R$_f$ 0.51 (chloroform/methanol, 1:3); R$_f$ 0.43 (1-butanol/water/acetic acid/ethyl acetate, 1:1:1:1); [α]D −41.04° (C=0.48; DMF); MS (FAB) 395 (M++H); AAA: Glu (0.97), His (1.08), Pro (1.00), analytical RP-HPLC (t$_R$=14.59 min; a linear gradient of 5–35% B over 30 min at a flow rate of 1.0 ml/min); $^{13}$C-NMR (DMSO-d$_6$; 30° C.); 169.8 (—CO-His), 171.9 (—CO-Pro), 205.0 (—CSNH—), 206.4 (—CSNH$_2$).

EXAMPLE 3

L-pyroglutamyl-L-histidyl-L-proline thioamide [Pro [CSNH]H³]TRH)

The title peptide was prepared from L-pyroglutamyl-(N$^{im}$-dinitrophenyl)-L-histidyl-L-proline amide (0.13 g, 0.22 mmol) and mercaptoethanol (1 ml) according to the procedure given for the synthesis of the compound of Example 1. Final purification was performed by reversed phase chromatography (Vydac C$_{18}$, 5% CH$_3$CN in 0.05% TFA in H$_2$O, flow 3.5 ml/min) and afforded the title product as a white, fluffy powder (33.4 mg, 40.1%); R$_f$ 0.47 (chloroform/methanol, 1:3); R$_f$ 0.39 (1-butanol/water/acetic acid/ethyl acetate, 1:1:1:1); MS (FAB) 379 (M++H); AAA: Glu (1.06), His (1.05), Pro (1.00); analytical RP-HPLC (t$_R$=9.99 min, a linear gradient of 5–35% B over 30 min at a flow rate of 1.0 ml/min); $^{13}$C-NMR (DMSO-d$_6$, 30° C.); 169.7 (—CO-His), 171.8 (—CO-Pro), 177.1 (—CO—NH—), 206.2 (—CSNH$_2$). A synthesis for this compound ([Pro [CSNH]H³]TRH) was previously reported by Kruszynski (1986).

EXAMPLE 4

L-thiopyroglutamyl [CSNH]L-norleucyl-L-prolinethioamide (Top [CSNH]Nle-Pro ψ [CSNH$_2$]

L-pyroglutamyl-L-norleucyl-L-proline amide (0.24 g, 0.7 mmol) was dissolved in freshly distilled THF (20 ml). To the stirred solution was added Lawesson's Reagent (0.32 g, 0.7 mmol) and the mixture was stirred at room temperature until starting materials were fully consumed (2 h, TLC control). Evaporation of the solvent in vacuo was followed by purification by flash chromatography using ethyl acetate. The final product was obtained using reversed phase chromatography (Vydac C$_{18}$, 32% CH$_3$CN in 0.05% TFA, flow 3.5 ml/min) which gave, after lyophilization, a white powder (108 mg, 41.9%): R$_f$ 0.72 (chloroform/methanol/acetic acid, 85:10:5) R$_f$ 0.24 (ethyl acetate); [α]D −116.0° (C=0.47); DMF); MS (FAB) 371 (M++H); AAA: Glu (1.02), Nle (0.87), Pro (1.00); analytical RP-HPLC (t$_R$=16.59 min; a linear gradient 25–55% B over 30 minutes at a flow rate of 1.0 ml/mn). The product was also analyzed by $^1$H and $^{13}$C NMR spectroscopy (DMSO-d$_6$, 30° C.) and gave spectra consistent with the expected structure. In particular, the presence of three thioamide peaks at δ200–210 and one amide peak at δ168 also confirm the structural integrity of this compound.

PHARMACOLOGY

Utilizing the following Materials and Methods, compounds encompassed within Formulae I and II were tested for TRH receptor binding properties.

Receptor Binding Assay

Adult, male Sprague-Dawley rats were obtained from Taconic Farms (Germantown, N.Y.) and housed at controlled temperature (22° C.) and light cycle (12/12 h) with free access to food and water. On the experimental day, six to eight animals were rapidly decapitated and their brains quickly removed and placed on a cold plate. Anterior pituitary and cortex tissue samples were obtained and processed immediately for receptor-binding experiments.

All steps of the tissue preparation and binding assays were done on ice. After weighing, pooled tissue samples were homogenized in 25 ml of ice-cold sodium phosphate buffer (0.1M, pH 7.4–7.5), using a Brinkmann Polytron homogenizer (setting 7, 15–20 s). The homogenates were then centrifuged in a refrigerated Sorvall RC5B centrifuge at 39000 g for 30 minutes. The supernatants were discharged and the pellets were resuspended to a concentration of 50 (pituitary) or 100 mg wet weight/ml (ww/ml, cortex) in ice-cold sodium phosphate buffer containing 177 μM Bacitracin.

Competition experiments were performed by incubating mixtures of tissue resuspensions, [3H][3-Me-His2]-TRH (87 Ci/mmol, Amersham) in 3 to 5 nM final concentration and increasing amounts of analog in a total volume of 100 μl/vial at 4° to 6° C. for 2.5 hours. In order to limit loss of peptides by adherence to glass, 0.05% bovine serum albumin was included in the assays. Nonspecific binding was determined in the presence of 10 μM TRH. The incubation period was terminated by vacuum filtration of the incubation mixture through Whatman GF/B glass filters, using a 48-well cell harvester (Brandel Inc., Gaithersburg, Md.), followed by four rinses with 4 ml each of ice-cold 0.9% NaCl solution. Filters were then placed in scintillation vials and kept overnight in 5 ml of watermiscible scintillation fluid (Beckman Ready-Solv™ HP) each. Bound radioactivity was measured after thorough shaking of the vials on the following day in an LKB 1218 Rackbeta liquid scintillation counter with automatic correction for tritium quenching. Specific binding was calculated as total binding minus nonspecific binding. Inhibition constants, Ki, were determined according to Cheng and Prusoff (1973) using the radioligand-binding analysis software LIGAND (Elsevier-Biosoft; Munson and Rodbard, 1980). Unless otherwise stated, data in tables and figures represent mean values±S.E.M. (standard error of the mean of separate experiments done in duplicate).

Results obtained in the above receptor binding assay for the compounds of Examples 1, 2 and 3, as well as TRH are shown in Table I below.

TABLE I

| Compound Tested | Binding K$_i$ (nM) | |
|---|---|---|
| | Pituitary | Cortex |
| TRH | 24.1 ± 14.2 | 26.1 ± 4.5 |
| Example 1 | 31.9 ± 2.9 | 501 ± 173 |
| Example 2 | 85.4 ± 17.8 | 86.1 ± 6.3 |

TABLE I-continued

| Compound Tested | Binding $K_i$ (nM) | |
| --- | --- | --- |
| | Pituitary | Cortex |
| Example 3 | 8.0 ± 0.2 | 93.1 ± 16.5 |

As may be seen from the results contained in Table I, the compounds of the present invention, Formulae I and II, possess highly selective binding properties for different TRH receptor sites in brain tissues. Based upon such results, it is considered that the compounds of the present invention possess pharmacologically advantageous properties which will allow them to be used effectively in the treatment of diverse physical conditions, including depression, circulatory shock, central nervous system ischemic damage, ALS, spinal cord injury and hypertension. In particular, it is believed that the results provided in Table I show that the thionated analogues of TRH encompassed by the present invention, can highly, selectively and differentially bind to different TRH receptors in animal tissues, and thus can provide a valuable tool in the treatment of diverse physical conditions such as those listed above. Furthermore, it is envisioned that such properties will allow the compounds of Formulae I and II to be used in a method of detecting and/or evidencing the presence of TRH receptor binding sites in animal tissues.

Suitable methods for determining the presence of thyrotropin releasing hormone receptor sites on animal tissues include, for example, procedures such as outlined above under the caption "Receptor Binding Assay". More generally, however, suitable methods for detecting TRH receptor binding sites which are encompassed herein, comprise the following steps:

(a) contacting an animal tissue with a compound of Formula I;
(b) measuring the amount of said compound which binds to said animal tissue; and
(c) correlating the amount of said compound which binds to said tissues to the detection of TRH receptors.

Procedures for performing each of the above steps (a)-(c) should be readily apparent to those of ordinary skill in the art of receptor binding assays. Moreover, they should be readily apparent to those of ordinary skill in the art based upon the present inventors' disclosures herein.

It is also envisioned that the the compounds of the present invention will be useful as diagnostic aids in the evaluation of hyperthyroid and hypothyroid states. In this regard, it is noted that the compounds of the present invention are able to affect the release of TSH [Lankiewicz et al (1990)], and some of the compounds of the present invention (e.g., Example 2) are even more potent than TRH in stimulating TSH release.

PHARMACEUTICAL COMPOSITIONS

In order to treat diverse physical conditions with the compounds of the present invention, there are also provided pharmaceutical compositions herein which contain an effective amount of a compound of Formula I, for treating a desired physical condition, such as ALS, hypertension, etc.

The compounds of this invention can be administered by oral, parenteral (intramuscular (i.m.), intraperitoneal (i.p.), intravenous (i.v.) or subcutaneous (s.c.) injection), nasal, vaginal, rectal or sublingual routes of administration and can be formulated in dosage forms appropriate for each route of administration.

Solid dosage forms for oral administration include capsules, tablets, pills, powders and granules. In such solid dosage forms, the active compound is mixed with at least one inert carrier such as sucrose, lactose, or starch. Such dosage forms can also comprise, as is normal practice, additional substances other than inert diluents, e.g., lubricating agents such as magnesium stearate. In the case of capsules, tablets and pills, the dosage forms may also comprise buffering agents. Tablets and pills can additionally be prepared with enteric coatings.

Liquid dosage forms for oral administration include emulsions, solutions, suspensions, syrups, the elixirs containing inert diluents commonly used in the art, such as water. Besides, such inert diluents, compositions can also include adjuvants, such as wetting agents, emulsifying and suspending agents, and sweetening, flavoring, and perfuming agents.

Preparations according to this invention for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants such as preserving, wetting, emulsifying, and dispersing agents. They may be sterilized by, for example, filtration through a bacteria-retaining filter, by incorporating sterilizing agents into the compositions, by irradiating the compositions, or by heating the compositions. They can also be manufactured in a medium of sterile water, or some other sterile injectable medium immediately before use.

Dosage levels of the Formula I compounds should be adequate to produce the desired physical effect on the patient. Accordingly, the dosage may be varied over a wide range. Daily dosages may range from about 0.03 to about 80 mg/kg of body weight, preferably from about 0.1 to about 40 mg/kg and most preferably from 0.5 to 30 mg/kg of body weight, according to the physical condition being treated.

Following are examples of representative dosage formulations.

| Ingredients | Amount (mg) |
| --- | --- |
| Tablet Formulation | |
| Formula I compound | 25 |
| Calcium phosphate | 120 |
| Lactose | 50 |
| Starch | 23 |
| Magnesium stearate | 1 |
| Injectable Solution | |
| Formula I compound | 1 |
| Sodium chloride | 9 |
| Distilled water q.s. → 1.0 ml | |

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

Literature References

1. Still, W. C. et al, *J Org. Chem.*, 43, 2923 (1978).

2. Moroder, L. et al, *Z. Physiol. Chem.*, 357, 1651 (1976).
3. Anderson, J. C. et al, *J. Chem. Soc.*, C1967, 108 (1967).
4. Hollosi, M. et al, *Acta Chim. Hung.*, 71, 101 (1972).
5. Kruszynski, M., *Pol. J. Chem.*, 60, 95 (1986).
6. Andersen, T. P. et al, *Liebigs Ann. Chem.*, 1986, 269 (1986).
7. Cheng, Y. et al, *Biochem. Pharmacol.*, 22, 3099 (1973).
8. Munson, P. J. et al, *Anal. Biochem.*, 107, 220 (1980).
9. Bordanszky, M. et al, *Peptide Synthesis*, 2nd Edition, John Wiley, N.Y. (1976).
10. Lankiewicz et al, *Proceedings of the Eleventh American Peptide Symposium*, U.S.A., p. 976-977 (1990).

What is claimed is:

1. A compound, having the formula:

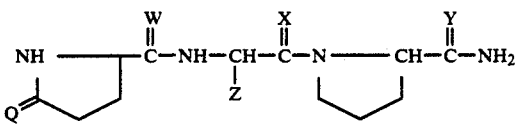

wherein
Q, W, X and Y, same or different, are oxygen or sulfur, with the proviso that at least one of Q, W and X is always sulfur;
Z is lower alkyl or (4-imidazolyl)methyl; and the pharmaceutically acceptable salts thereof.

2. The compound of claim 1, wherein said compound is L-thiopyroglutamyl-L-histidyl-L-proline amide, or a pharmaceutically acceptable salt thereof.

3. The compound of claim 1, wherein said compound is L-thiopyroglutamyl-L-histidyl-L-proline thioamide, or a pharmaceutically acceptable salt thereof.

4. The compound of claim 1, wherein said compound is L-thiopyroglutamyl$\psi$[CSNH]L-norleucyl-L-proline thioamide, or a pharmaceutically acceptable salt thereof.

5. A pharmaceutical composition, comprising:
(a) an effective amount of an active compound having the formula:

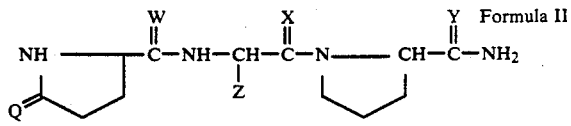

wherein,
Q, W, X and Y, same or different, are oxygen or sulfur, with the proviso that at least one of Q, W, and X is always sulfur;
Z is lower alkyl or (4-imidazolyl)methyl; and the pharmaceutically acceptable salts thereof;
(b) a pharmaceutically acceptable carrier thereof.

6. The pharmaceutical composition of claim 5, wherein the active compound is L-thiopyroglutamyl-L-histidyl-Lproline amide, or a pharmaceutically acceptable salt thereof.

7. The pharmaceutical composition of claim 5, wherein the active compound is L-thiopyroglutamyl-L-histidyl-L-proline thioamide, or a pharmaceutically acceptable salt thereof.

8. The pharmaceutical composition of claim 5, wherein the active compound is L-thiopyroglutamyl $\psi$ [CSNH] L-norleucyl-L-proline thioamide, or a pharmaceutically acceptable salt thereof.

9. A compound selected from the group consisting essentially of:
L-thiopyroglutamyl-L-histidyl-L-proline amide;
L-thiopyroglutamyl-L-histidyl-L-thioamide;
L-thiopyroglutamyl$\psi$[CSNH]L-norleucyl-L-proline thioamide; and
pharmaceutically acceptable salts thereof.

10. A pharmaceutical composition, comprising:
(a) an effective amount of a compound recited in claim 9; and
(b) a pharmaceutically acceptable carrier therefor.

* * * * *